United States Patent
Ferrer

(10) Patent No.: US 12,233,288 B1
(45) Date of Patent: Feb. 25, 2025

(54) MOTION BASED METHODS FOR COSMETIC ULTRASOUND TREATMENTS

(71) Applicant: Sibel Ferrer, Houston, TX (US)

(72) Inventor: Sibel Ferrer, Houston, TX (US)

(73) Assignee: Venusa Group LLC, Austin, TX (US)

( * ) Notice: Subject to any disclaimer, the term of this patent is extended or adjusted under 35 U.S.C. 154(b) by 0 days.

(21) Appl. No.: 18/405,852

(22) Filed: Jan. 5, 2024

Related U.S. Application Data

(60) Provisional application No. 63/532,783, filed on Aug. 15, 2023.

(51) Int. Cl.
*A61N 7/00* (2006.01)

(52) U.S. Cl.
CPC ........ *A61N 7/00* (2013.01); *A61N 2007/0034* (2013.01)

(58) Field of Classification Search
CPC .......................... A61N 7/00; A61N 2007/0034
See application file for complete search history.

(56) References Cited

U.S. PATENT DOCUMENTS

| | | | | |
|---|---|---|---|---|
| 2008/0146970 A1* | 6/2008 | Litman | ..................... | A61N 7/02 601/2 |
| 2008/0195003 A1* | 8/2008 | Sliwa | ....................... | A61N 7/02 601/3 |
| 2008/0214966 A1* | 9/2008 | Slayton | ............... | G01S 15/8909 601/3 |
| 2010/0249669 A1* | 9/2010 | Ulric | ....................... | A61N 7/02 601/2 |
| 2012/0016239 A1* | 1/2012 | Barthe | ................. | A61B 8/4272 600/439 |
| 2017/0028227 A1* | 2/2017 | Emery | ................... | G10K 11/30 |

* cited by examiner

*Primary Examiner* — Hien N Nguyen
(74) *Attorney, Agent, or Firm* — Jeffrey L. Streets

(57) ABSTRACT

Some embodiments provide a method including applying high-intensity focused ultrasound energy to a skin treatment area with simultaneous movement of the transducer body across the skin treatment area to form a pattern of treatment lines in tissue at a first depth below the surface of the skin. For example, the pattern of treatment lines may be formed by the movement of the transducer body during one or more treatment cycles. A preferred pattern of treatment lines includes treatment lines that intersect. Furthermore, the method may further include applying the high-intensity focused ultrasound energy to the skin treatment area with simultaneous movement of the transducer body across the skin treatment area to form a second pattern of treatment lines in tissue at a second depth below the surface of the skin and a third pattern of treatment lines in tissue at a third depth below the surface of the skin.

20 Claims, 10 Drawing Sheets

MOTION BASED METHODS FOR COSMETIC ULTRASOUND TREATMENTS

BACKGROUND

The present disclosure relates to ultrasound therapy methods, and in particular to ultrasound therapy methods for use in noninvasive cosmetic tissue manipulation.

Background of the Related Art

Sagging of skin and facial muscles often manifests itself in individuals over time in a process commonly known as aging. This sagging can be the result of the effects of gravity and also from changes in the connective tissue that occur as a person ages. Recently, the use of high-intensity focused ultrasound systems has gained popularity as a therapeutic treatment to reduce the sagging of skin and facial muscles. High-intensity focused ultrasound treatments are preferred by some individuals over more invasive surgical treatments like a facelift to tighten facial tissues. These ultrasound treatments have been used to treat various areas of a patient's skin, such as the cheeks, neck, eyebrows, under chin region/area and décolletage (chest area).

High-frequency ultrasound systems, such as the Ulthera® ultrasound system, are able to provide a targeted, precise, local heating capable of inducing ablation (thermal injury) to underlying skin and subcutaneous fat using sound waves at a frequency from about 20 MHz to 500 MHz or more. A high-frequency ultrasound system targets the deep, foundational layers of the skin with focused ultrasonic energy to produce heat and stimulate new collagen formation. The tissue layers targeted in these high-frequency ultrasound systems may include the same layers that a surgeon would target in a surgical facelift procedure. Examples of such prior art high frequency ultrasound systems and methods of use are disclosed in U.S. Pat. Nos. 7,758,524 and 8,366,622, which are hereby incorporated by reference.

High-frequency ultrasound systems direct and focus acoustic waves to a selected treatment depth below the surface of the skin. The energy from the focused acoustic waves will produce heat within the tissue at the selected treatment depth as a result of friction during energy absorption, producing discrete points of stimulation or burns in the tissue. Some immediate improvement in the appearance of the skin may occur, such as by the shrinkage of existing collagen or the coagulation of various proteins. The body's healing response may also lift the treated tissue over time. For example, fibroblasts may form additional proteins, such as collagen and elastin, to repair and support the tissue, which in turn lifts the tissue over time. Importantly, the focusing of the acoustic energy at a desired depth within the skin tissue means that heat can be generated at the desired depth without significant effect on the skin tissue above or below the desired depth. Different transducers are available, where each transducer focuses the acoustic energy at a different depth.

In spite of its non-invasive nature, high-frequency ultrasound treatments are well-known for having undesirable side effects. For example, known side effects potentially include erythema (redness), edema (swelling), welting (a localized area of linear visible edema), pain, tenderness, bruising, nerve effects, transient local muscle weakness, transient numbness, and burns/scarring. Because of these undesirable side effects, many patients opt to only treat small areas. Typically, the longer the treatment, the more pain is experienced. Furthermore, performing a high-frequency ultrasound treatment directly over a bone, like the jawline, tends to produce more discomfort than treatment of other areas.

BRIEF SUMMARY

Some embodiments provide a method comprising applying high-intensity focused ultrasound energy to a skin treatment area with simultaneous movement of the transducer body across the skin treatment area to form a pattern of treatment lines in tissue at a first depth below the surface of the skin.

DETAILED DESCRIPTION

Figure 1:
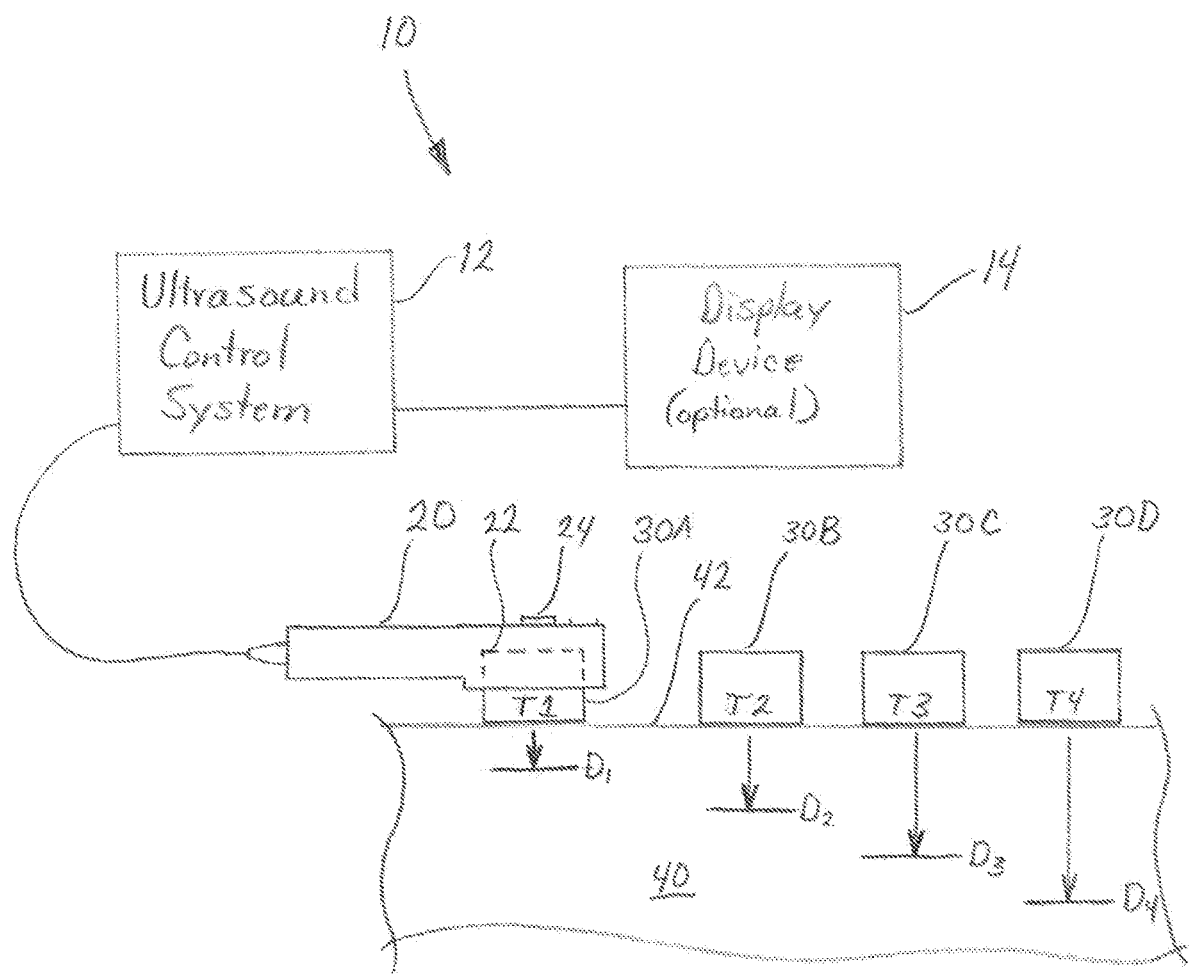
FIG. 1 is a diagram of a high-intensity focused ultrasound system.

Some embodiments provide a method comprising applying high-intensity focused ultrasound energy to a skin treatment area with simultaneous movement of the transducer body across the skin treatment area to form a pattern of treatment lines in tissue at a first depth below the surface of the skin.

In some embodiments, the high-intensity focused ultrasound energy is applied to a skin treatment area using a high-intensity focused ultrasound treatment system. One such system includes a handpiece, one or more transducers, a control system and an optional display device. A transducer is a device that converts energy from one form to another. In an ultrasound treatment system, electrical energy is converted to sound waves by a material that exhibits the piezoelectric effect. The transducer may have various transducer configurations. For example, the transducer can be configured as a dedicated therapy transducer, as a combined dual-mode imaging and therapy transducer, as coupled or co-housed imaging and therapy transducers, or as a therapy transducer and separate imaging transducer. The control system can also comprise various configurations for controlling transducer and system functionality, including for example a microprocessor with software and a plurality of input/output devices, a system for controlling electronic and/or mechanical scanning and/or multiplexing of transducers, a system for power delivery, systems for monitoring, systems for sensing the spatial position of the transducer, and systems for handling user input and recording treatment results, among other features. The high-intensity focused ultrasound system is preferably configured for providing ultrasound treatment to a patient such that one or more of the epidermis, dermis, adipose, superficial muscular aponeurosis system (SMAS), and/or muscle tissue layers can be treated in a noninvasive fashion with minimal side effects and, in particular, minimal pain and/or downtime. An exemplary high-intensity focused ultrasound system comprises a control system, handpiece, and one or more transducer configured to provide treatment to one or more selected depths or layers. A suitable high-intensity focused ultrasound treatment system is available from Ulthera, Inc.

A skin treatment area is any surface area of the skin that is targeted for treatment using high-intensity focused ultrasound. While the treatment area may be an area of a patient's face, the treatment area may be any selected area of skin on a patient's body. For example, the treatment area may be, without limitation, the forehead, eyebrows, around the eyes, eye lids, temple case areas, nose, lips and surrounding areas, chin, cheeks (i.e., mustache to ear), chin, double chin, neck, decolletage, chest and all areas of the body including the legs, knees, under arms, hands, forearm, abdomen, and the feminine vulva. A skin treatment area may be flat or arced according to the contour of the body in the selected treatment area. While acknowledging that skin covers many body parts with different shapes, skin may be discussed, in generalized terms, as having a two-dimensional surface or "area" (i.e., length and width) and a thickness.

The transducer is the component of the system that converts electrical energy into acoustic energy. For example, the transducer may include one or more piezoelectric devices or elements that emit ultrasound energy at a given frequency, where the intensity of the electrical energy input to the piezoelectric devices may be controlled to vary the intensity of the ultrasound every that is emitted. An acoustic lens may be used to concentrate ultrasound energy at a focal point that is a known distance (depth) from the acoustic lens. A transducer body may secure and house the one or more transducers, one or more acoustic lenses, and any associated mechanical and electrical components for securing and operating the one or more transducers and the one or more acoustic lenses. The transducer body has a skin-contacting face that is directed toward a patient's skin in a selected treatment area so that the high-intensity focused ultrasound energy is directed into the skin. A thin film of ultrasound gel is preferably applied to the skin in the treatment area prior to applying the high-intensity focused ultrasound energy.

The transducer body is mechanically and electrically connected to a handpiece that is adapted for gripping in the hand of a user, which may be an aesthetician. The handpiece may be positioned and moved to control the position, orientation and/or movement of the transducer relative to the skin in the treatment area. The handpiece may also be used to convey a force on the transducer body, such that the transducer body may be held against the skin with a desired amount of pressure. Furthermore, the handpiece may include control elements, such as a button, for initiating a treatment cycle.

A treatment cycle is a period, interval or duration of time during which high-intensity focused ultrasound energy is being emitted from the transducer body. A treatment cycle may be initiated by, for example, pressing a button on the handpiece. A treatment plan for a given treatment area may include any number of treatment cycles, such as 10 to 20 or more treatment cycles. The duration of time, the intensity of the focused ultrasound energy, and other parameters associated with the emission of high-intensity focused ultrasound energy during a treatment cycle may be controlled by the control system. The duration, intensity and other parameters may be fixed or user-selectable through a user interface to the control system.

In some embodiments, the design of the one or more transducers with the transducer body, as well as the control program executed by the control system, may cooperate to cause high-intensity focused ultrasound energy to be emitted from the transducer body at one or more emission points along a longitudinal axis of the face of the transducer body that is to be placed against the skin. These one or more emission points, such as 5 to 10 emission points, may be established by an equal number of piezoelectric and acoustic lens devices that are fixed in position or by one or more piezoelectric and acoustic lens devices that are mechanically driven along the longitudinal axis of the transducer body during a treatment cycle. A transducer body that includes piezoelectric and acoustic lens devices at each emission point may support simultaneous emission of high-intensity focused ultrasound energy from any one (an individual), several (a group) or all of the emission points at any point in time during the treatment cycle, including emission from all emission points throughout the duration of the treatment cycle. Conversely, a transducer body having a single set of piezoelectric and acoustic lens devices that is mechanically driven along the longitudinal axis of the transducer body can only emit high-intensity focused ultrasound energy from a single emission point at a time, perhaps with some pause there between for the set of devices to be moved to the next emission point in a sequence.

In some embodiments, the system may include a plurality of transducer bodies that may be interchangeably secured to the handpiece for use in a skin treatment. Each of the transducer bodies may be configured to have a different focal length or depth of skin penetration to treat different target layers or tissues. A particular transducer body may be selected to focus high-intensity focused ultrasound energy at a point having a predetermined depth below a skin surface in the treatment area. Without limitation, the plurality of transducer bodies may include a first transducer body that focuses the ultrasound energy at a predetermined depth of 4.5 millimeters (mm), a second transducer body that focuses the ultrasound energy at a predetermined depth of 3.0 mm, and a third transducer body that focuses the ultrasound energy at a predetermined depth of 1.5 mm. The plurality of transducer bodies may include a greater or lesser number of transducer bodies and the depth associated with any one or more of the transducer bodies may be different from those specifically identified. In a non-limiting example, the plurality of transducer bodies may include a first transducer body configured to deliver focused ultrasound at a depth of 1.5 mm that may be used to form a treatment line in an epidermis layer of the skin, a second transducer configured to deliver focused ultrasound at a depth of 3.0 mm that may be used to form a treatment line in a dermis layer, adipose layer and/or SMAS layer of the skin, and/or a transducer body configured to deliver focused ultrasound at a depth of 4.5 mm that may be used to form a treatment line in a muscle layer just below the skin.

In accordance with various embodiments, a given treatment cycle may be performed under substantially continuous and constant motion of the transducer body. A treatment cycle begins when the transducer is turned on to provide high-intensity focused ultrasound energy into tissue below the surface of a patient's skin and ends when the transducer is turned off. Typically, the treatment cycle is initiated by the user manually pressing a button on the handpiece and the treatment cycle continues for a duration controlled by the control system. The handpiece may include one or more finger-operative buttons to enable a user to easily control the initiation of a treatment cycle with one finger of the same hand that is manipulating the handpiece. The control system may control the duration of a treatment cycle, which may be accompanied by an audible indicator so that the user can time their movement of the handpiece so that the transducer is moved from, for example, one boundary of the treatment area to an opposing boundary of the treatment area during the treatment cycle. Specifically, if a treatment cycle lasts some fixed period of time, such as about 3 seconds, the audible sound would have a duration of about 3 seconds to inform the user that ultrasound energy is being emitted. For a given treatment area, the aesthetician may then move the transducer body through a continuous movement across the treatment area at a speed that causes the transducer to be at one end or boundary of the treatment area when the treatment cycle begins and to be at an opposing end or boundary of the treatment area when the treatment cycle automatically concludes. The transducer is preferably moved at a speed that is relatively constant and preferably does not include pauses of movement at any point during the treatment cycle.

In some embodiments, the transducer body has a longitudinal axis and emits the high-intensity focused ultrasound energy from multiple points along the longitudinal axis. Using such a transducer body, the handpiece is preferably moved so that the longitudinal axis of the transducer body is held substantially perpendicular to a direction of the movement of the transducer body. For example, if the direction of transducer body movement (i.e., the path) is vertical, then the handpiece is preferably held so that the longitudinal axis of the transducer body is horizontal (i.e., perpendicular to the path). Similarly, if the direction of transducer body movement (i.e., the path) is an upward-to-the-left at a 45 degree angle, then the handpiece is preferably held so that the longitudinal axis of the transducer body is upward-to-the-right at a 45 degree angle (i.e., perpendicular to the path). Note that positioning the longitudinal axis of the transducer body "upward-to-the-right at a 45 degree angle" is the same as positioning the longitudinal axis "downward-to-the-left at a 45 degree angle." However, the orientation of the transducer body may be either with the proximal end of the transducer body (i.e., the end nearest the hand grip portion of the handpiece) "upward-to-the-right at a 45 degree angle" or the distal end of the transducer (i.e., the end furthest from the hand grip portion of the handpiece). Where the transducer body has multiple emission points that emit ultrasound energy in a sequence (perhaps from one end to the other end), the orientation of the transducer body may affect the pattern of treatment lines that are formed during a treatment cycle (i.e., from left-to-right in one orientation and from right-to-left in another orientation). Where the path of transducer movement is in a straight line and the transducer body movement may be substantially translational (i.e., movement with little or no rotation). However, if the path of transducer movement is curved, the transducer body may be rotated slightly, such as to keep the longitudinal axis of the transducer body perpendicular to the path.

The term "line", as used herein, is synonymous with "line segment" and means a straight or curved trace of a point moving from a starting point to an ending point. While a line may have a regular or irregular width or cross-sectional shape, a line may be described primarily by its length and its path. As used herein, a "treatment line" is a line created by the movement of a point of focused ultrasound moving through tissue. For example, one or more treatment lines may be created at a given depth or tissue layer below the surface of a patient's skin by moving a transducer body across the surface of the skin during a treatment cycle.

A pattern of treatment lines includes any two or more (i.e., a plurality) treatment lines in the same treatment area. A pattern may include treatment lines that are parallel or not parallel and/or treatment lines that intersect or do not intersect. Embodiments may form a pattern of treatment lines by performing one or more treatment cycles in a given treatment area using a given transducer (having a given focal distance or depth). Optionally, a pattern of treatment lines may be formed at each of a plurality of depths, which may include a pattern of treatment lines in each of a plurality of tissue layers. For example, a pattern of treatment lines may be formed with each of a plurality of transducers (each having a different focal distance or depth) within the given treatment area. The pattern of treatment lines formed with each of the transducers (i.e., at each depth) may be the same or different. Without limitation, each pattern of treatment lines may have the same or different number of treatment lines, the same or different combination of directions or pathways of the treatment lines, the same or different length of treatment lines, and/or the same or different intensity used to form the treatment lines.

In some embodiments, the pattern of treatment lines may be formed by the movement of the transducer body during each of a plurality of treatment cycles. In one example, the plurality of treatment cycles may include at least one treatment cycle with simultaneous movement of the transducer body along a first path across the treatment area and at least one treatment cycle with simultaneous movement of the transducer body along a second path across the treatment area. Optionally, the second path may cross the first path to form treatment lines that intersect. The pattern of treatment lines may be a grid. Still further, for each of the plurality of treatment cycles, a plurality of treatment lines may be formed during the individual treatment cycle, wherein the treatment lines are spaced apart relative to a longitudinal axis of the transducer body. Optionally, the plurality of first treatment lines formed during a treatment cycle may also be spaced apart in a direction of the transducer body movement.

Embodiments apply the high-intensity focused ultrasound energy in a manner that will stimulate collagen production along the one or more treatment lines in the treatment pattern. It is believed that the high-intensity focused ultrasound energy causes heat at the focal point of the emission points of the selected transducer body. Without being limited to a particular theory, this heat may cause shrinkage of existing collagen and/or other tissues at the focal point or otherwise stimulate activity of fibroblasts that repair, reinforce and/or replace the existing collagen with additional collagen. The response to the high-intensity focused ultrasound is shrinking, tightening and/or smoothing of the collagen-containing tissue layer with a corresponding improvement in the appearance of the skin, which may manifest as less sagging and/or fewer wrinkles. Accordingly, the methods may be used as a non-invasive cosmetic treatment. Without limitation, an ultrasonic treatment piezoelectric device may be configured to focus ultrasound energy at a depth in a range between 3 mm and 9 mm below a skin surface with a treatment frequency in a range of 1 MHz to 10 MHz at an acoustic power in a range of 1 watt to 100 watts. Optionally, the high-intensity focused ultrasound energy may have a frequency from about 1 MHz to about 500 MHZ.

In embodiments, after applying high-intensity focused ultrasound energy to a skin treatment area with simultaneous movement of the transducer body across the skin treatment area to form a pattern of treatment lines in tissue at a first depth below the surface of the skin, the method may further comprise applying high-intensity focused ultrasound energy to the skin treatment area with simultaneous movement of the transducer body across the skin treatment area to form a pattern of treatment lines in tissue at a second depth below the surface of the skin. In a further option, the method may continue to form a pattern of treatment lines at any number of depths. For example, the method may further comprise applying high-intensity focused ultrasound energy to the skin treatment area with simultaneous movement of the transducer body across the skin treatment area to form a pattern of treatment lines in tissue at a third depth below the surface of the skin. In one option, the pattern of treatment lines at each of the first, second and third depths may be formed by the movement of the transducer body during a plurality of treatment cycles. The pattern of treatment lines preferably includes a plurality of treatment lines that intersect. In a further option, at each of the first, second and third depths, the plurality of treatment cycles may include at least one treatment cycle with movement of the transducer body along a first path across the skin treatment area and at least one treatment cycle with movement of the transducer body along a second path across the skin treatment area, wherein the second path crosses the first path to form a plurality of treatment lines that intersect. For example, a pattern of interconnected lines may intersect at perpendicular angles (about 90 degrees) or at various acute angles (less than about 90 degrees) or obtuse angles (greater than about 90 degrees). Optionally, the pattern of treatment lines at any one or more of the depths may be a grid.

In some embodiments, the method may further comprise holding the transducer body an angle relative to the surface of the skin and pressing the transducer body firmly against the skin during movement of the transducer body so that tissue is forced to rise up ahead of the transducer body during a treatment cycle.

In some embodiments, the method may further comprise applying pressure to the skin above a nerve in or near the treatment area during the treatment cycle. Applying pressure in this manner during a treatment cycle may reduce patient discomfort. For example, an aesthetician may manipulate the handpiece with one hand and apply pressure to the patient's skin with the other hand. It is believed that pressing or massaging pressure points can activate or relax nerves in the muscles so that the nerves send signals to the central nervous system that reduce sensations of pain. Optionally, while pressing the pressure points, the skin may also be pulled in a direction away from the treatment area and/or toward the root of the nerve.

It should be recognized that for any given combination of the high-intensity focused ultrasound energy level and the duration of a treatment cycle, any given tissue will be exposed to less energy if the transducer body is moving during the treatment cycle than if the transducer body is stationary. Furthermore, any given tissue will be exposed to less energy when the transducer body is moving quickly along a path than when the transducer body is moving slowly along the path. Accordingly, the method may further comprise adjusting the treatment cycle duration and/or ultrasound energy level based on the size of the treatment area. For example, the treatment cycle duration may be extended at the same ultrasound energy level so that the transducer speed may be kept constant yet able to cover a longer path (i.e., in a larger treatment area) during a treatment cycle. In another example, the ultrasound energy level may be increased while keeping the same duration of treatment cycle so that the transducer speed may be increased to cover a longer path during the treatment cycle with the same amount of energy per unit of distance being applied to the tissue. In yet other examples, both the treatment cycle duration and the energy level may be adjusted to accommodate certain transducer body speeds and distances during a treatment cycle.

Some embodiments that stimulate the muscles may provide a benefit of causing the muscles to return to a more youthful position. In addition to the improved appearance, restoring a more youthful position to certain muscles in the vicinity of a lymphatic node may, in turn, release or open the lymphatic node that was being obstructed by pressure from the muscle. Improving the functioning of the lymphatic system in this manner may result in the release or draining of toxins that accumulate over time due to the blockage caused by the facial muscles. It is believed that the lymphatic system is stimulated as a result of the heat produced by the ultrasound such that the nodes are opened. Furthermore, vibrations and movements performed by massage in the direction of the lymphatic drains during the treatment are believed to help drain toxins and reduce inflammation and liquid retention in the face.

Some embodiments may provide the technical benefit of increasing the life of the transducer body. By moving the transducer body during a treatment cycle, a greater amount of area may be treated during a given treatment cycle. Each treatment cycle causes some degree of wear on the transducer elements (i.e., the piezoelectric devices), such that a transducer body is typically replaced after a setpoint number of treatment cycles. So, if a treatment area can be treated with fewer treatment cycles by moving the transducer body during each treatment cycle compared to keeping the transducer body stationary during each treatment cycle, then the life of the transducer body is effectively extended or increased.

Embodiments are believed to provide the technical benefit of improved skin appearance and less discomfort by applying the high-intensity focused ultrasound with simultaneous movement of the transducer body across at least a portion of the treatment area during the treatment cycle compared with maintaining the transducer body in a fixed or stationary position during the treatment cycle. It is believed that the treatment lines cause collagen repair and/or enhancement to occur along the treatment lines, which results in an improved collagen matrix compared to the isolated treatment points formed by a transducer body that is held in a fixed or stationary position during the treatment cycle. Furthermore, the reduced intensity of the ultrasound at any given point in the tissue as a result of the movement is believed to reduce or eliminate the level of discomfort that is experienced during a treatment cycle with a fixed or stationary transducer body. Accordingly, the high-intensity focused ultrasound energy may be applied to a skin treatment area of a patient with simultaneous movement of the transducer body across the skin treatment area such that the patient remains comfortable without taking sedation, medication, or laughing gas.

In certain embodiments, the disclosed methods and systems may be used to perform a noninvasive face lift and deep tissue tightening. For example, a treatment may include treating the SMAS layer by delivering high-intensity focused ultrasound energy at a depth, distribution, duration, and energy level to achieve a desired therapeutic effect. Furthermore, the treatment may target the outer muscle layer, SMAS layer, the dermis layer, and/or the epidermis layer. In some embodiments, a treatment with the high-intensity focused ultrasound may target an array of foci, a locus of foci, a line focus, and/or diffraction patterns from single element, multiple elements, annular array, one-, two-, or three-dimensional arrays, broadband transducers, and/or combinations thereof, with or without lenses, acoustic components, mechanical and/or electronic focusing to treat the one or more layer of tissue at fixed and/or variable depth or dynamically controllable depths and positions.

Embodiments disclosed herein relating to high-intensity focused ultrasound treatments are only limited examples provided to enhance understanding of the disclosed methods and systems and are not intended to limit the scope of the embodiments. For example, the principles, features and methods discussed may be applied to any medical procedure, other tissues, or other treatment applications. For example, the principles, features, and methods discussed may be applied to any superficial muscular aponeurosis system (SMAS)-like muscular fascia, such as platysma, temporal fascia, and/or occipital fascia, or any other medical application. Further, various aspects of the embodiments may be suitably applied to other applications. In accordance with various aspects of the embodiments, a method and system for noninvasive face lifts and deep tissue tightening are provided.

In the description of the drawings, references are made to the accompanying drawings which illustrate specific exemplary embodiments. It should be understood that these embodiments are exemplary (i.e., non-limiting examples) and that structural and procedural changes may be made without deviating from the scope of the embodiments. The drawings and description, therefore, are not to be taken as limiting the scope of the disclosure and claims. Embodiments may be realized by any number of hardware devices and components configured to perform the specified functions.

FIG. 1 is a diagram of a high-intensity focused ultrasound system 10. The system 10 includes a control system 12, an optional display device 14, a handpiece 20, and a set of transducer bodies 30A-D. The control system 12 may be configured to control and operate one or more transducers within a selected one of the transducer bodies 30A-D to provide a treatment. The handpiece 20 includes a dock 22 into which any one of the various transducers 30A-D may be interchangeably received and operated. The control system 12 provides electrical power to the currently installed transducer 30A to perform a treatment cycle. A treatment cycle may be initiated by a user pressing a button 24 on the handpiece 20. Each of the transducers 30A-D may provide ultrasound energy that is focused a different depth or penetration into the target tissue 40. For example, the set of transducers may include a first transducer 30A configured to focus high-intensity ultrasound at a first depth ($D_1$), such as 1.5 mm below the surface 42 of the skin and/or muscle tissue 40; a second transducer 30B configured to focus high-intensity ultrasound at a second depth ($D_2$) such as 3.0 mm; a third transducer 30C configured to focus high-intensity ultrasound at a third depth ($D_3$) such as 4.5 mm; and a fourth transducer 30D configured to focus high-intensity ultrasound at a fourth depth ($D_4$) such as 6.0 mm.

The control system 12 may comprise an electronic drive and control unit including a drive circuit, power supply and other electronic control devices that are configured to control the operation of any one of the transducers installed in the handpiece. The control system may be a personal computer or any other conventional processing unit. The system 10 may also comprise an input/output device, such as a keyboard, mouse, touchscreen, or any other device for transmitting or receiving information to and from the control system 12. Furthermore, the control system 12 may receive operating data from the handpiece 20 and/or the installed transducer body. Optionally, the system 10 may be configured to display ultrasound imaging on the display device 14. The display device may be a monitor, LCD screen, or any other device configured to display an image. The display device may be used to visualize delineations between tissue layers of the skin and/or bones, muscles, vessels or nerves in any one or more treatment area.

The system 10 may be configured to utilize a combined dual-mode imaging/therapy transducer, coupled or co-housed imaging/therapy transducers, or simply a separate therapy transducer and an imaging transducer. The imaging feature allows the user to visualize the skin and sub-dermal layers of interest before treatment to assure delivery of the ultrasound energy to a targeted structure and/or layer of interest. In certain of these embodiments, the system 10 may be configured for treating a selected layer of tissue (e.g., SMAS) by imaging the selected layer of tissue and displaying the image on the display device 14. The image may be helpful for localization of the treatment area and surrounding structures, followed by delivery of ultrasound energy at a desired depth, distribution, timing, and energy level to achieve the desired therapeutic effect. Optionally, the treatment area may be monitored before, during, and after therapy to assess the results and/or provide feedback.

Treatment of one or more tissue and/or fascia, such as the epidermis, dermis, adipose, SMAS and muscle layers, can be achieved by the systems and methods. The system may be used to perform a high-intensity focused ultrasound treatment to tighten or shrink patient tissue by heating a targeted skin or muscle layer (i.e., causing minor thermal damage or injury) in the treatment area. Shrinkage of collagen fibers through ultrasound treatment and repair of collagen fibers after the ultrasound treatment may be used to tighten sagging or stretched tissue throughout a treatment area.

Figure 2:
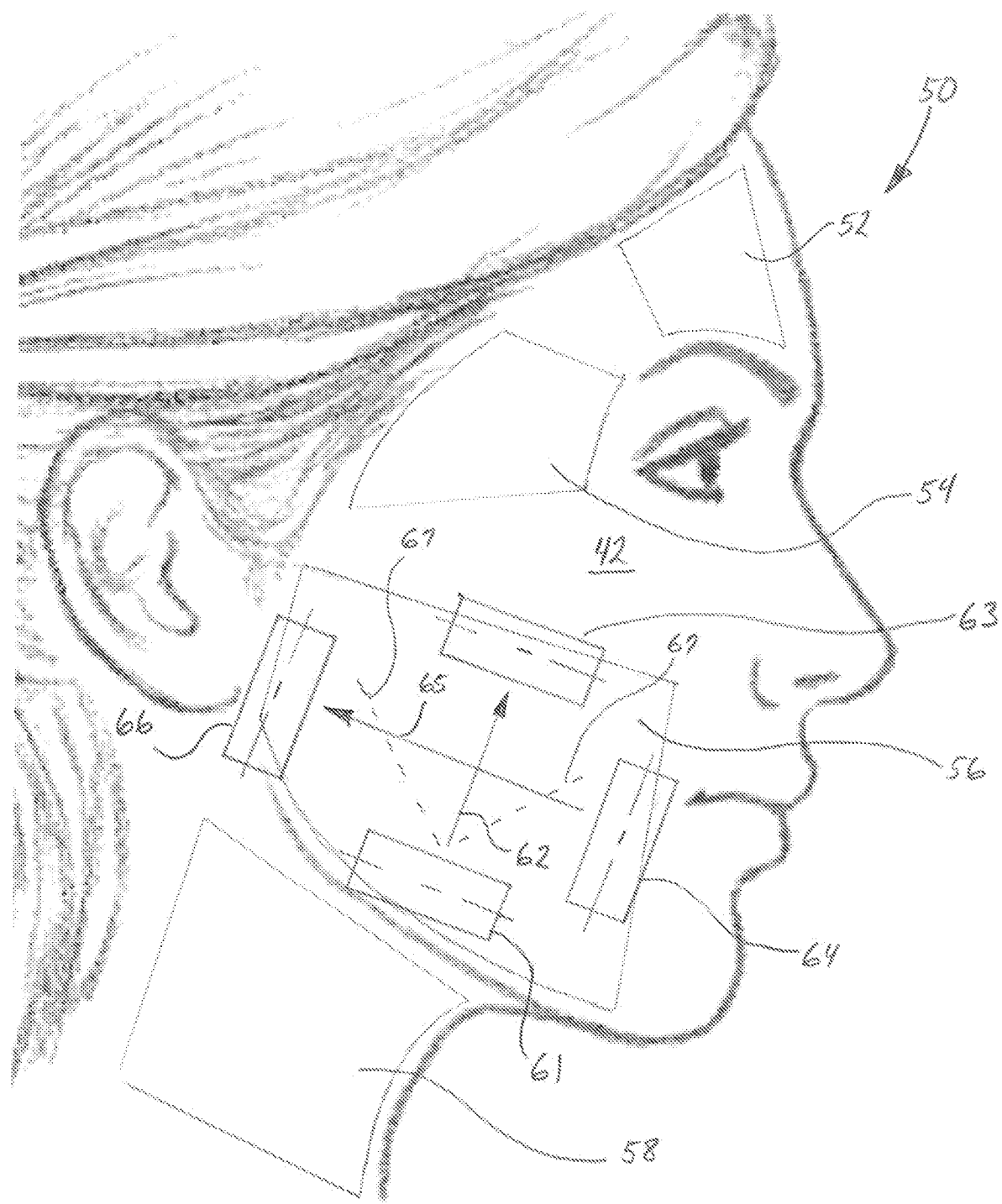
FIG. 2 is a diagram of a face illustrating several potential treatment areas, including a first path and a second path for a transducer body across a treatment area of the cheek.

FIG. 2 is a diagram of a patient's face 50 illustrating several potential treatment areas on the skin 42. The illustrating treatment areas include a forehead area 52, a temple area 54, a check area 56, and a neck area 58. Any of these areas or other areas may be treated using the disclosed embodiments. Using the check area 56 ("treatment area") as an example for further discussion, a basic treatment plan is shown. The basic treatment plan illustrates a first treatment cycle that should include a starting position 61 for a transducer body footprint or face (shown as a rectangle), a directional path 62 for movement of the transducer body during the treatment cycle, and an ending position 63 for the transducer body footprint or face. This first treatment cycle may be described as having a path that is generally vertical, such that any one or more treatment lines formed during the treatment cycle will be generally vertically oriented.

This basic treatment plan also illustrates a second treatment cycle that should include a starting position 64 for a transducer body footprint or face (shown as a rectangle), a directional path 65 for movement of the transducer body during the treatment cycle, and an ending position 66 for the transducer body footprint or face. This second treatment cycle may be described as having a path that is generally horizontal, such that any one or more treatment lines formed during the treatment cycle will be generally horizontal oriented. The first path 62 and the second path 65 for a transducer body cross the treatment area 56 of the check to form a treatment pattern (not shown). It is expected that the illustrated basic treatment plan may form intersecting treatment lines. A more detailed treatment plan might include additional treatment cycles with movement of the transducer body along a generally vertical path to the left and/or the right of the first path 62 and/or movement of the transducer body along a generally horizontal path above and/or below the second path 65 in order to provide more complete coverage of the treatment area 56. Still further, embodiments may include these or other treatment plans at one or more other depths, which may be implemented using one or more other transducer bodies 30A-D (see FIG. 1)

Note that the transducer body (illustrated as rectangle) is moved in lateral directions 62, 65 that are generally perpendicular to the illustrated longitudinal axis of the transducer body in each treatment cycle of the treatment plan. While the lateral movement is preferably perpendicular, the lateral direction of the movement may be at up to 45 degrees in either direction of perpendicular (see dashed lines 67 relative to the perpendicular path 62) without causing too much energy deliver in too small of an area. However, the transducer is preferably not moved in the longitudinal direction such that the plurality of ultrasound emission points would all pass along the same line and cause a much greater amount of stimulation/heating along that line.

Figure 3A:
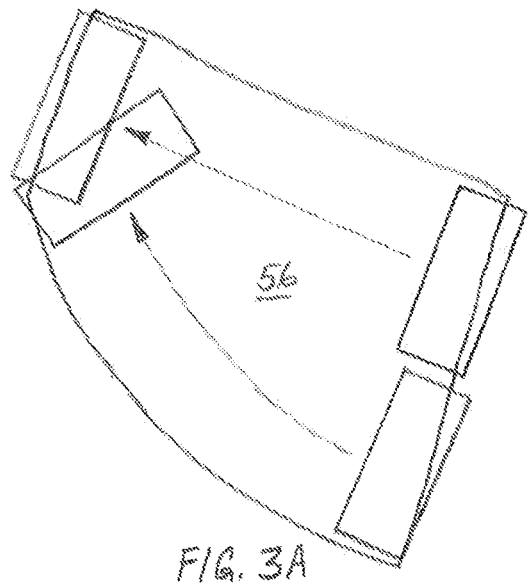
FIGS. 3A-B are diagrams of a treatment plan for a first treatment area.
Figure 3B:
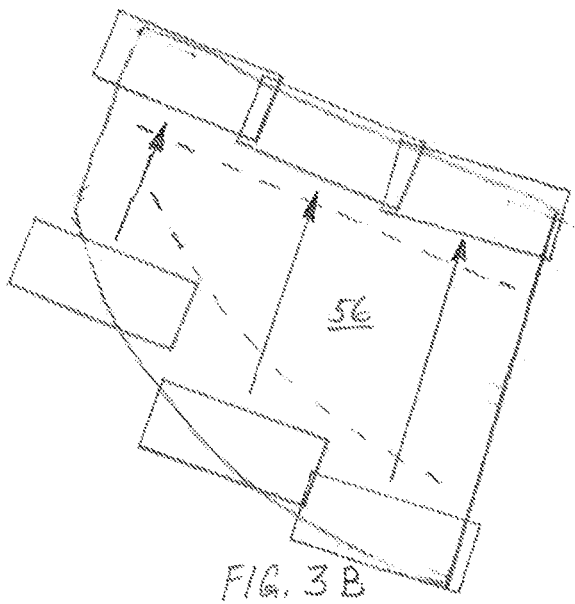

FIGS. 3A-B are diagrams of an alternative treatment plan for the first treatment area 56. FIG. 3A shows two adjacent treatment cycles from right to left covering the treatment area and FIG. 3B shows three adjacent treatment cycles from bottom to top covering the treatment area. These five treatment cycles are expected to form treatment lines in the same direction as the illustrated paths of the transducer body, such that the resulting treatment pattern will include several treatment lines, where at least a couple of the treatment lines may intersect.

Figure 4A:
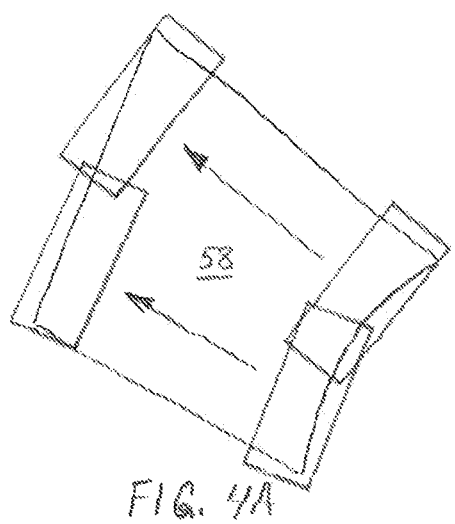
FIGS. 4A-B are diagrams of a treatment plan for a second treatment area.
Figure 4B:
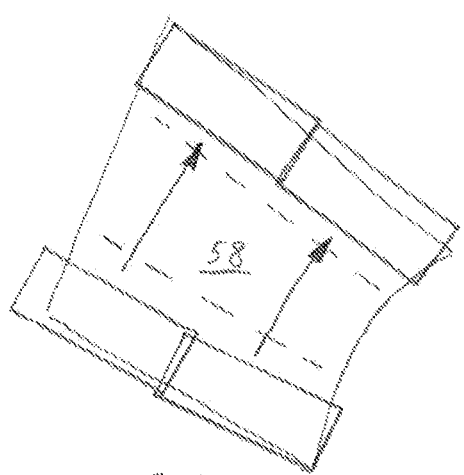

FIGS. 4A-B are diagrams of a treatment plan for a second treatment area 58 that has less area than the first treatment area 56 and a slightly different orientation or shape than the first treatment area. Accordingly, FIG. 4A shows two adjacent treatment cycles from lower right to upper left covering the second treatment area and FIG. 4B shows two adjacent treatment cycles from lower left to upper right covering the treatment area. These four treatment cycles are expected to form treatment lines in the same direction as the illustrated paths of the transducer body, such that the resulting treatment pattern will include several treatment lines, where at least a couple of the treatment lines may intersect.

Figure 5A:
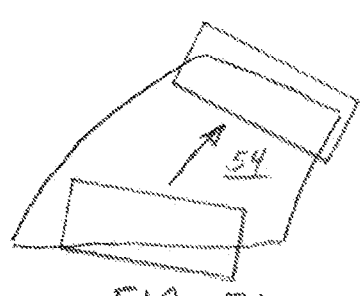
FIGS. 5A-B are diagrams of a treatment plan for a third treatment area.
Figure 5B:
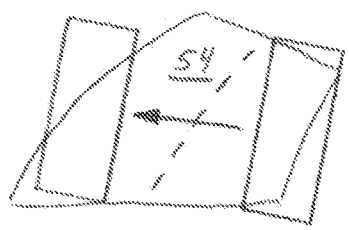

FIGS. 5A-B are diagrams of a treatment plan for a third treatment area 54 that has even less area than the second treatment area 58 and a narrower shape than the second treatment area. Accordingly, FIG. 5A shows one treatment cycle from lower left to upper right covering the third treatment area and FIG. 5B shows one treatment cycle from right to left covering the treatment area. These two treatment cycles are expected to form treatment lines in the same direction as the illustrated paths of the transducer body, such that the resulting treatment pattern will include multiple treatment lines, where at least a couple of the treatment lines may intersect.

Figure 6A:
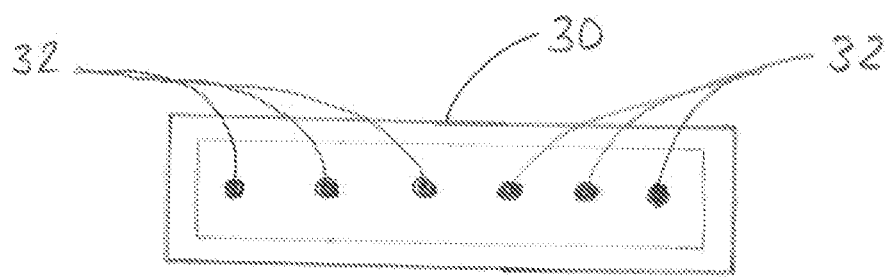
FIG. 6A is a diagram of a transducer having six high-intensity focused ultrasound energy point sources.

FIG. 6A is a diagram of the skin-contacting footprint or face of a transducer body 30 having six high-intensity focused ultrasound energy point sources. This footprint would be directed against the surface 42 of the skin (see FIG. 1) so that the emission points 32 (six shown) are positioned to emit the high-intensity ultrasound energy into the tissue 40 (see FIG. 1).

Figure 6B:
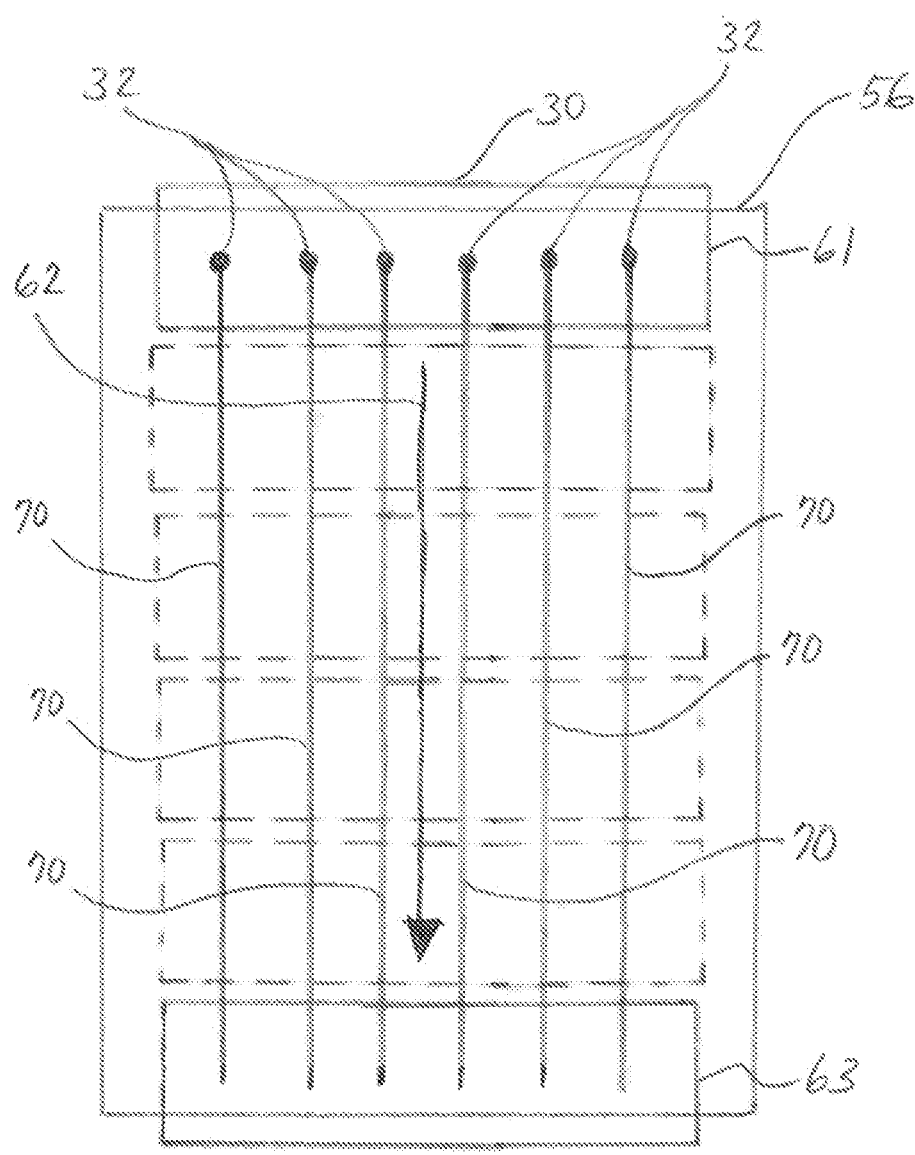
FIG. 6B is a diagram of six treatment lines formed by moving the transducer across a treatment area with all six of the point sources turned on for the duration of a treatment cycle.

FIG. 6B is a diagram of six treatment lines 70 that are formed by moving the transducer body 30 across a treatment area 56 (See FIG. 2) with all six of the emission points 32 turned on (activated) for the duration of a treatment cycle. With further reference to FIGS. 2 and 6B, the treatment cycle includes the starting position 61 for the transducer body 30 footprint or face (shown as a rectangle), the directional path 62 for movement of the transducer body 30 during the treatment cycle, and the ending position 63 for the transducer body 30 footprint or face. The illustrated treatment cycle forms the six treatment lines 70 corresponding to the six emission points 32 being moved along path 62 during the treatment cycle.

Figure 6C:
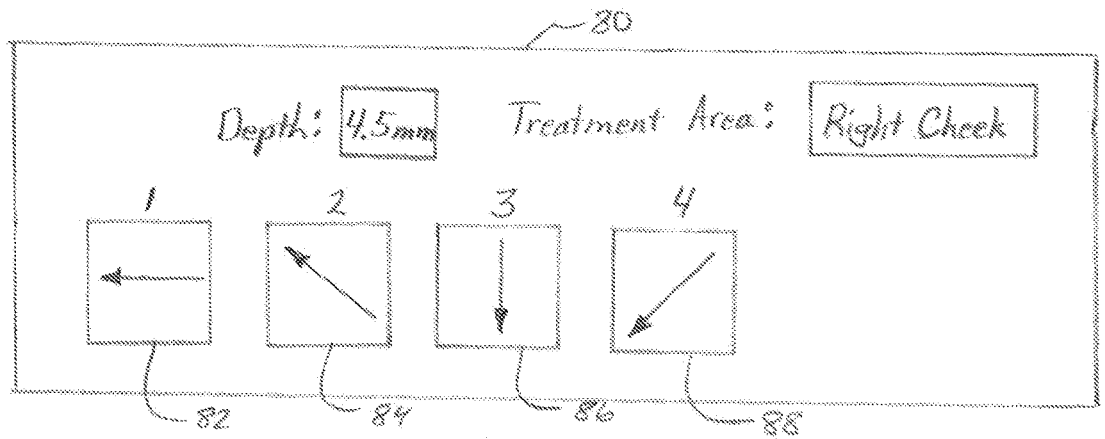
FIG. 6C is a diagram of a treatment plan for a selected treatment area at a selected depth.

FIG. 6C is a diagram of a treatment plan 80 for a selected treatment area at a selected depth. The treatment plan 80 is for treating a right check (the "treatment area") at a depth of 4.5 mm using four treatment cycles. One treatment cycle 82 is to be performed from right to left through the treatment area, one treatment cycle 84 is to be performed from lower right to upper left through the treatment area, one treatment cycle 86 is to be performed from top to bottom through the treatment area, and yet another treatment cycle 88 is to be performed from upper right to lower left through the treatment area. Additional treatment cycles could also be performed, such as repeating the identified treatment cycles 82, 84, 86, 88. The manual positioning and movement of the handpiece and transducer body will have some variation such that the additional treatment cycles may provide additional opportunities for collagen growth, such as along the additional treatment lines which may or may not be intersecting lines.

Figure 6D:
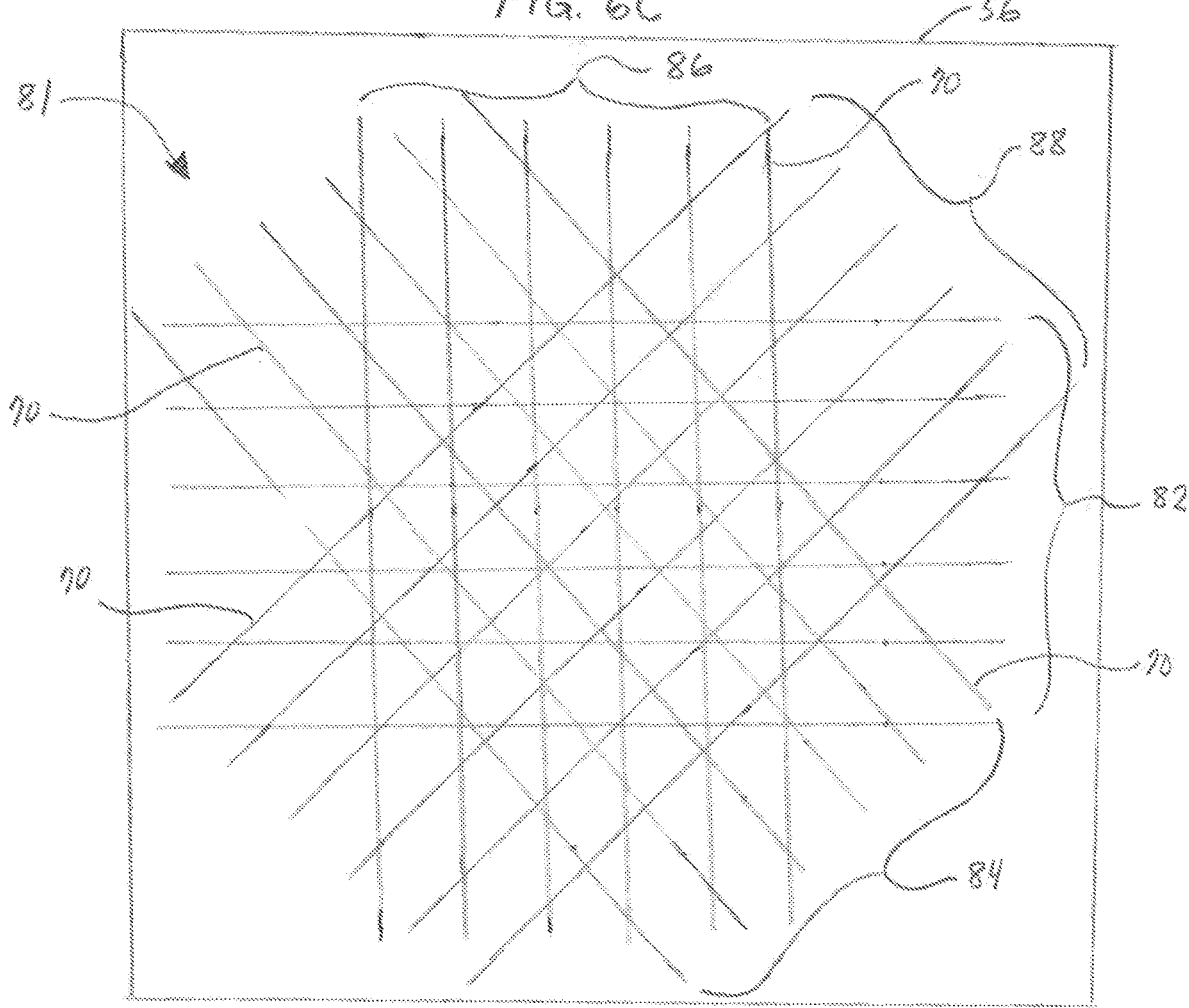
FIG. 6D is a diagram of the treatment lines formed at the selected depth as a result of performing the treatment cycles with the indicated movement (FIG. 6B) of the transducer body (FIG. 6A) in accordance with the treatment plan (FIG. 6C).

FIG. 6D is a diagram of the treatment area 56 including the treatment pattern 81 that has numerous treatment lines 70 formed at the selected depth as a result of performing the treatment cycles 82, 84, 86, 88 with the indicated movement (FIG. 6B) of the transducer body 30 (FIG. 6A) with six emission points 32 in accordance with the treatment plan 80 (FIG. 6C). The treatment pattern 81 may be described as a grid having numerous intersecting treatment lines. These long interconnected or intersecting treatment lines may provide better support for the creation of collagen and interactions with the underlying muscle than does an array of spaced-apart treatment points or spots. A treatment line is interconnected with another treatment line when the two treatment lines cross or intersect each other at the same depth within the skin. The interconnection of the treatment lines provides a cross-linked scaffolding of newly developing extra-cellular matrix proteins such as collagen. The treatment pattern 81 may be formed in tissue at any one or more depth below the skin surface. For example, at a depth of 4.5 mm, the high-intensity focused ultrasound ("HIFU") may serve to lift the structure of the muscles so that they return to a more youthful position.

Figure 7A:
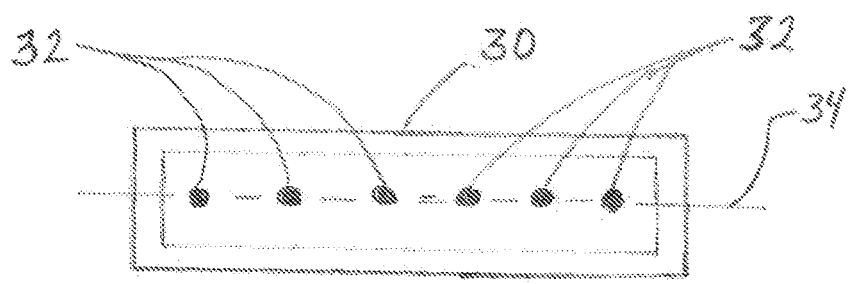
FIG. 7A is a diagram of a transducer having six high-intensity focused ultrasound energy point sources.

FIG. 7A is a diagram of the skin-contacting footprint or face of a transducer body 30 having six high-intensity focused ultrasound energy point sources or emission points 32. This footprint would be directed against the surface 42 of the skin (see FIG. 1) so that the emission points 32 (six shown) are positioned to emit the high-intensity ultrasound energy into the tissue 40 (see FIG. 1). However, unlike the transducer body according to FIGS. 6A-D, the transducer body 30 of FIG. 7A-D emits high-intensity focused ultrasound energy from only one emission point 32 at a time, such as beginning with the left-most emission point 32 and then, in turn, each emission point 32 from left to right along the longitudinal axis 34. It should be recognized that the transducer body 30 may be manually reoriented 180 degrees of rotation such that the same sequence of activating the emission points 32 from left to right may then operate as a sequence from right to left without any change in control of the transducer body.

Figure 7B:
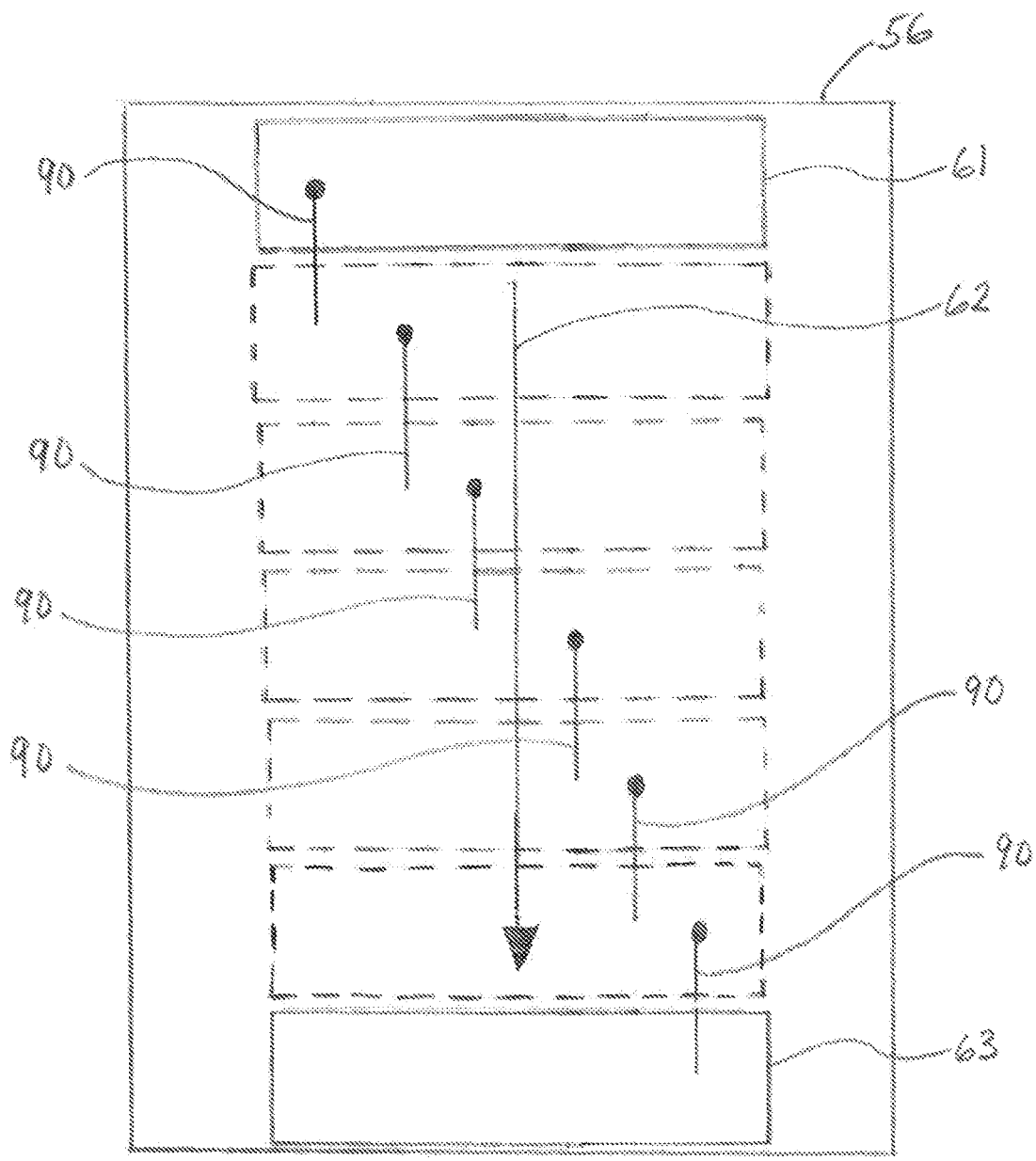
FIG. 7B is a diagram of six treatment lines formed by moving the transducer across a treatment area with the six point sources turned on/off in a sequence during the duration of a treatment cycle.

FIG. 7B is a diagram of six treatment lines 90 formed by moving the transducer 30 (as described in reference to FIG. 7A) across the treatment area 56 (See FIG. 2) with the six emission points 32 turned on (activated) one at a time in a left to right sequence during a treatment cycle. With further reference to FIGS. 2 and 7B, the treatment cycle includes the starting position 61 for the transducer body 30 footprint or face (shown as a rectangle), the directional path 62 for movement of the transducer body 30 during the treatment cycle, and the ending position 63 for the transducer body 30 footprint or face. The illustrated treatment cycle forms the six treatment lines 90 corresponding to the position of each of the six emission points 32 being moved along path 62 and activated in sequence during the treatment cycle. For example, if there are six emission points 32 that are each activated in sequence for the same amount of time immediately following the previous emission point, then the treatment cycle may form the six treatment lines 90. As shown, these treatment lines 90 are spaced-apart relative to the longitudinal axis 34 of the transducer body 30 (left to right as shown in FIG. 7B) as well as spaced apart or end to end from top to bottom of the treatment area 56. The treatment lines 90 are shorter than the treatment lines 70 in FIGS. 6B and 6D, but still provide much better skin restoration than does individual treatment points or spots.

Figure 7C:
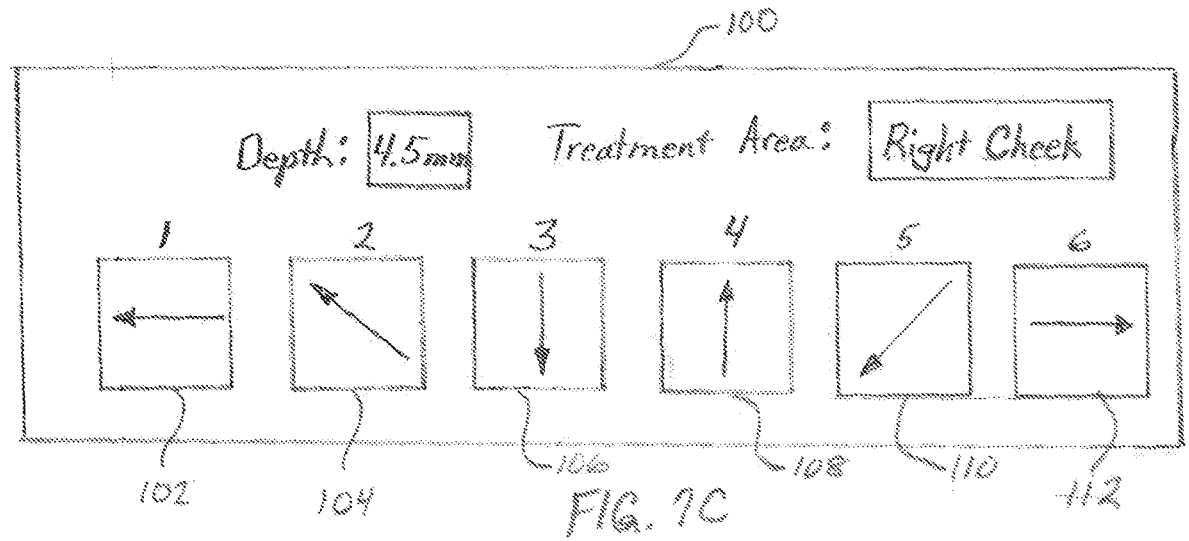
FIG. 7C is a diagram of a treatment plan for a selected treatment area at a selected depth.

FIG. 7C is a diagram of a treatment plan 100 for a selected treatment area at a selected depth. The treatment plan 100 is for treating a right cheek (the "treatment area") at a depth of 4.5 mm using six treatment cycles. One treatment cycle 102 is to be performed from right to left through the treatment area, one treatment cycle 104 is to be performed from lower right to upper left through the treatment area, one treatment cycle 106 is to be performed from top to bottom through the treatment area, one treatment cycle 108 is to be performed from bottom to top, one treatment cycle 110 is to be performed from upper right to lower left through the treatment area, and yet another treatment cycle 112 is to be performed from left to right. Additional treatment cycles could also be performed, such as repeating any of the identified treatment cycles 102, 104, 106, 108, 110, 112. The manual positioning and movement of the handpiece and transducer body will have some variation such that the additional treatment cycles may provide additional opportunities for collagen growth, such as along the additional treatment lines which may or may not be intersecting lines.

Figure 7D:
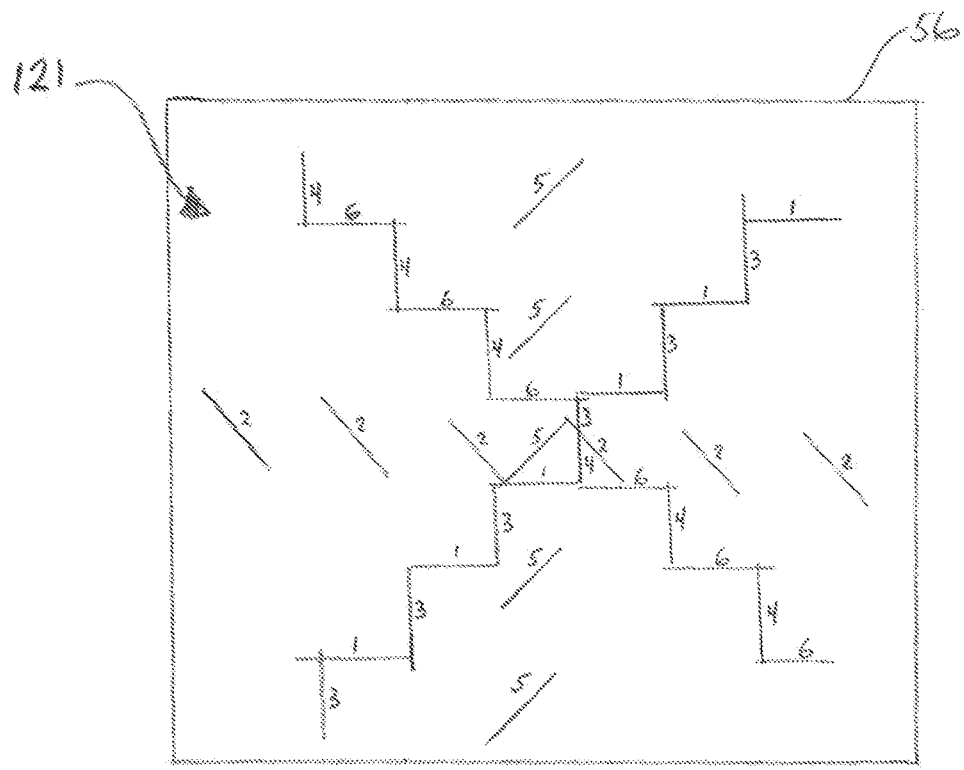
FIG. 7D is a diagram of the treatment lines formed at the selected depth as a result of performing the treatment cycles with the indicated movement (FIG. 7B) of the transducer body (FIG. 7A) in accordance with the treatment plan (FIG. 7C).

FIG. 7D is a diagram of the treatment area 56 including the treatment pattern 121 that has numerous treatment lines 90 formed at the selected depth as a result of performing the six treatment cycles 102, 104, 106, 108, 110, 112 with the indicated movement (FIG. 7B) of the transducer body 30 (FIG. 7A) with six sequentially activated emission points 32 in accordance with the treatment plan 100 (FIG. 7C). The treatment pattern 121 has numerous treatment lines, wherein some are intersecting with other treatment lines and others are not intersecting.

These interconnected or intersecting treatment lines, as well as completely separate treatment lines, may provide better support for the creation of collagen and interactions with the underlying muscle than does an array of spaced-apart treatment points or spots. A treatment line is interconnected with another treatment line when the two treatment lines cross or intersect each other at the same depth within the skin. The interconnection of the treatment lines provides a cross-linked scaffolding of newly developing extra-cellular matrix proteins such as collagen. The treatment pattern 121 may be formed in tissue at any one or more depth below the skin surface. For example, at a depth of 4.5 mm, the high-intensity focused ultrasound ("HIFU") may serve to lift the structure of the muscles so that they return to a more youthful position.

Figure 8:
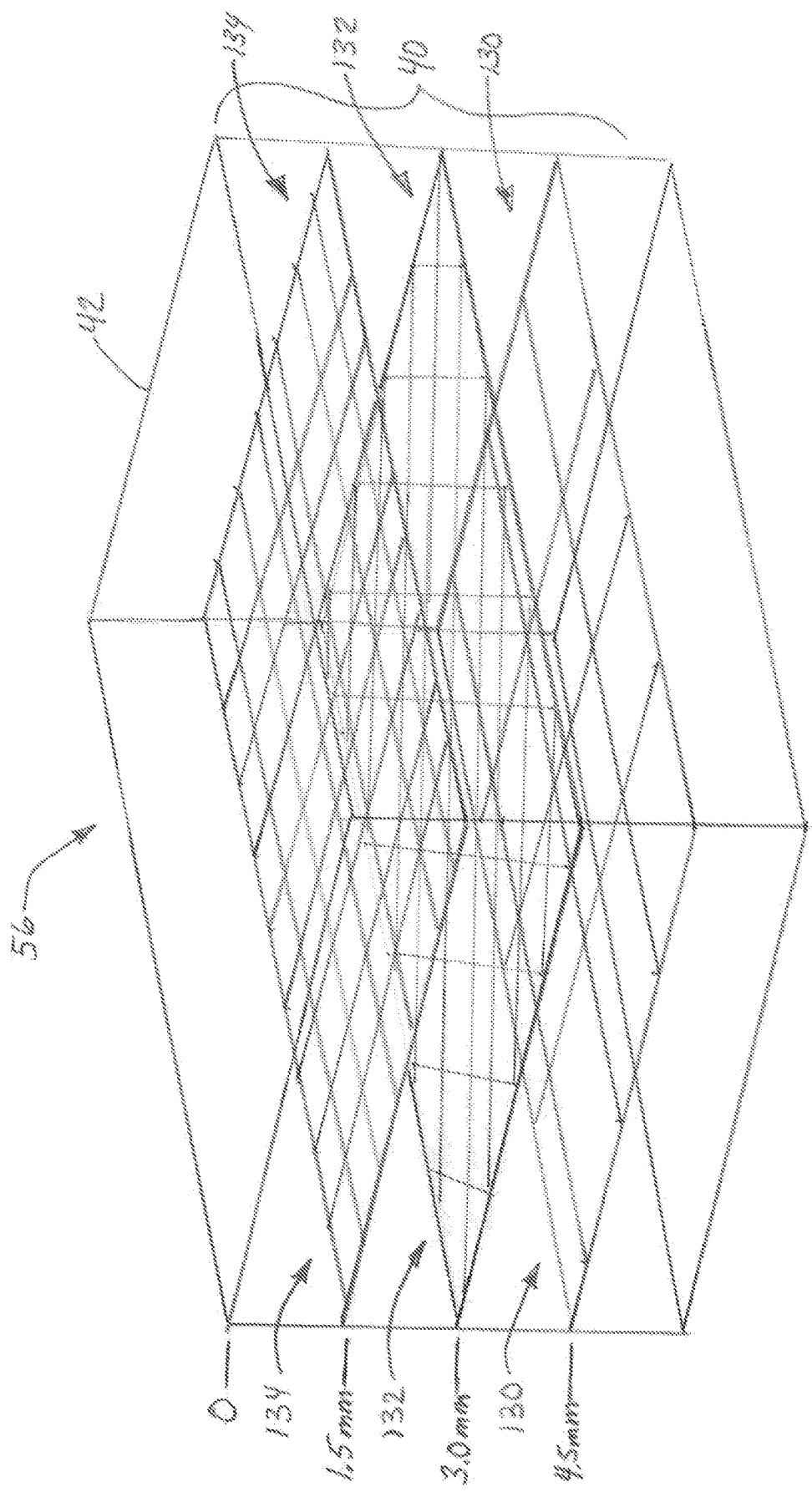
FIG. 8 is a diagram of tissue below the surface of the skin in a treatment area that has been treated to form a treatment pattern at three different depths.

FIG. 8 is a diagram of tissue 40 below the surface 42 of the skin in the treatment area 56 that has been treated to form a treatment pattern at three different depths. A user may treat the treatment area 56 with a high-intensity focused ultrasound system using a first transducer that targets a depth of 4.5 mm, a second transducer that targets a depth of 3.0 mm, and a third transducer that targets a depth of 1.5 mm. For example, the treatment area 56 has been treated with ultrasound energy focused at a depth of 4.5 mm to form a first treatment pattern 130, treated with ultrasound energy focused at a depth of 3.0 mm to form a second treatment pattern 132, and treated with ultrasound energy focused at a depth of 1.5 mm to form a third treatment pattern 134. The pattern of lines in each treatment pattern 130, 132, 134 are shown to be different, but each treatment pattern could be the same. Furthermore, the pattern of lines in each treatment pattern 130, 132, 134 are shown to have interconnected treatment lines, but the treatment lines could be separated. Still further, the treatment patterns 130, 132, 134 are shown as grids with perpendicular treatment lines, but a grid or any pattern of interconnected lines may have treatment lines that intersect at perpendicular angles (about 90 degrees), various acute angles (less than about 90 degrees) and/or obtuse angles (greater than about 90 degrees).

Figure 9B:
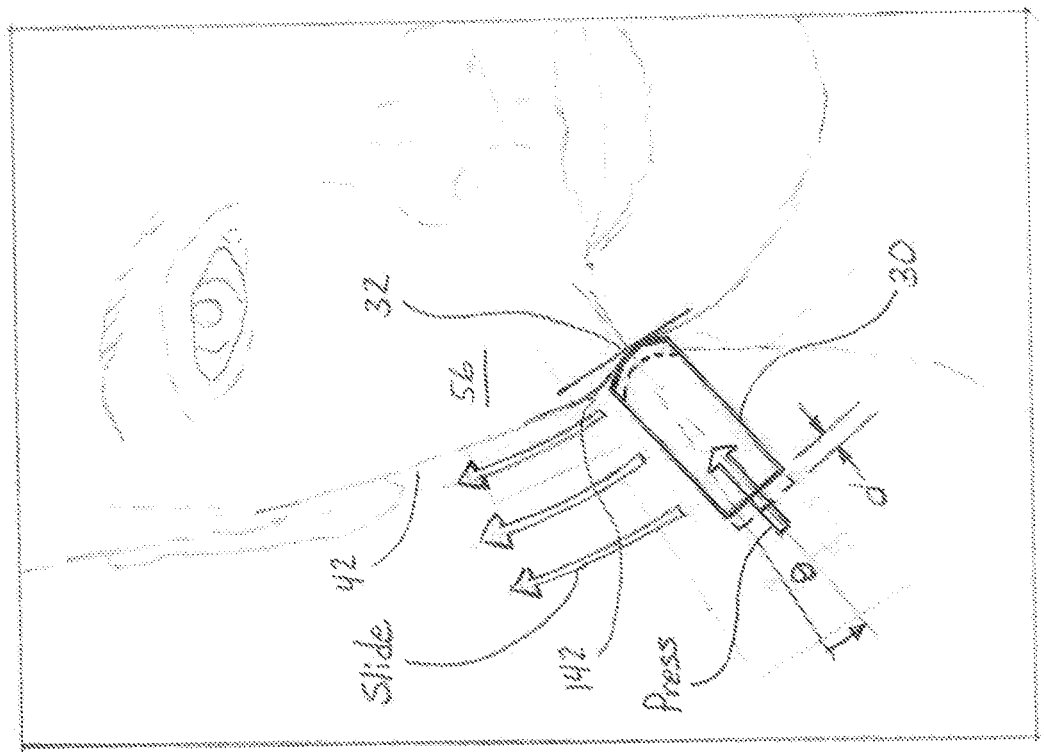
FIGS. 9A-B are diagrams illustrating a facial treatment area targeted with ultrasound energy with the transducer pressed against the skin at an angle relative to the surface of the skin.
Figure 9A:
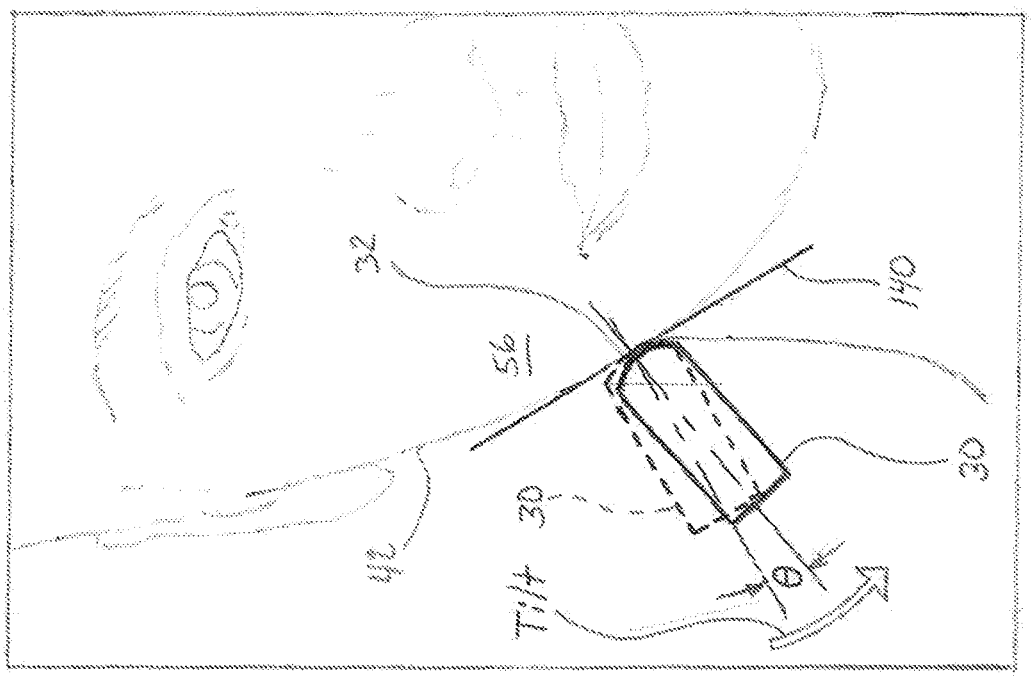

FIGS. 9A-B are diagrams illustrating a facial treatment area targeted with ultrasound energy with the footprint or face of the transducer body 30 pressed against the skin surface 42 at an angle relative to the surface of the skin. In FIG. 9A, the face of the transducer body 30, which includes the emission points 32, is touching the skin surface 42 in the treatment area 56. While the skin may not be perfectly flat, a tangent line 140 to the curve of the skin may serve as a reference for the angle of the transducer body 30 to the skin. The dashed outline is used to illustrate the transducer body 30 held perpendicular to the skin surface 42 (i.e., the tangent line 140). According to the technique of FIGS. 9A-B, the transducer body 30 is then tilted away from perpendicular by an angle ("Θ") so that the face of the transducer body is at a similar angle to the skin surface 42 (i.e., the tangent line 140). In FIG. 9B, the transducer body 30 is held at this angle and pressed into the skin 42 by some distance ("d"). While maintaining the angle of the transducer body 30 relative to the skin surface 42 and the pressure of the transducer body 30 against the skin surface 42, a treatment cycle may begin with simultaneous movement or sliding of the transducer body 30 across the treatment area 56. Note that the proximal end of the transducer body 30 is tilted back or away from the intended direction of movement. Accordingly, the skin surface 42 is allowed or encouraged to rise up (see point 142) ahead of the moving transducer body 30 with the emission points 32 angled slightly forward into the lifted skin 42.

Figure 10:
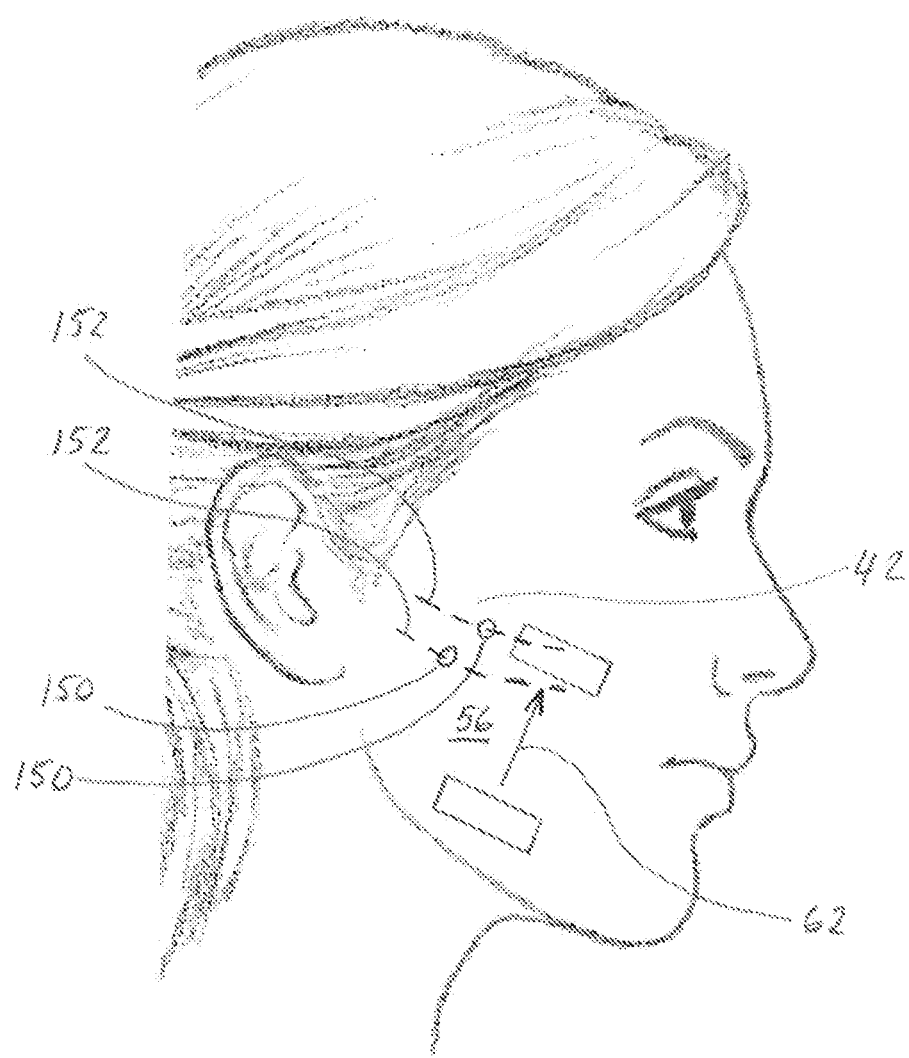
FIG. 10 is a diagram of a face illustrating an intended path for a transducer body during a treatment cycle and a pair of pressure points that may be pressed during the treatment cycle.

FIG. 10 is a diagram of a face illustrating an intended path 62 for the transducer body during a treatment cycle and a pair of pressure points 150 that may be pressed during the treatment cycle. For example, the pair of pressure points 150 may be selected according to the known position of certain facial nerves 152 (illustrated with dashed lines) in or near the treatment area 56. Physical pressure may be applied to the pressure points 150 on the skin surface 42 during a treatment cycle either to provide support or reduce discomfort. For example, a user may manipulate the handpiece and transducer with one hand and apply pressure to the patient's skin at pressure points 150 with two fingers of their other hand. In one preferred technique, pressure is applied to the skin directly over a facial nerve in or near the treatment area. Applying pressure to and/or massaging the pressure points can activate or relax nerves in the muscles so that the nerves send signals to the central nervous system that reduce sensations of pain. Optionally, while pressing the pressure points, the skin may also be pulled in a direction away from the treatment area and/or toward the root of the nerve (i.e., upward to the left as illustrated in FIG. 10).

The invention disclosed herein has been described with reference to various exemplary embodiments, however, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. These and other changes or modifications are intended to be included within the scope of the present invention, as set forth in the following claims.

As will be appreciated by one skilled in the art, embodiments may take the form of a system, method or computer program product. Accordingly, embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments may take the form of a computer program product embodied in one or more computer readable medium(s) having computer readable program code embodied thereon.

Any combination of one or more computer readable storage medium(s) may be utilized. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device. Furthermore, any program instruction or code that is embodied on such computer readable storage media (including forms referred to as volatile memory) that is not a transitory signal are, for the avoidance of doubt, considered "non-transitory".

Program code embodied on a computer readable storage medium may be transmitted using any appropriate medium, including but not limited to wireless, wireline, optical fiber cable, RF, etc., or any suitable combination of the foregoing. Computer program code for carrying out various operations may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, or as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Embodiments may be described with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, and/or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored on computer readable storage media is not a transitory signal, such that the program instructions can direct a computer, other programmable data processing apparatus, or other devices to function in a particular manner, and such that the program instructions stored in the computer readable storage medium produce an article of manufacture.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in any flowchart and/or block diagram block or blocks.

Flowcharts and block diagrams may be included in the Figures to illustrate the architecture, functionality, and operation of possible implementations of systems, methods and computer program products. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to limit the scope of the claims. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, components and/or groups, but do not preclude the presence or addition of one or more other features, integers, steps, operations, elements, components, and/or groups thereof. The terms "preferably," "preferred," "prefer," "optionally," "may," and similar terms are used to indicate that an item, condition or step being referred to is an optional (not required) feature of the embodiment.

The corresponding structures, materials, acts, and equivalents of all means or steps plus function elements in the claims below are intended to include any structure, material, or act for performing the function in combination with other claimed elements as specifically claimed. Embodiments have been presented for purposes of illustration and description, but it is not intended to be exhaustive or limited to the embodiments in the form disclosed. Many modifications and variations will be apparent to those of ordinary skill in the art after reading this disclosure. The disclosed embodiments were chosen and described as non-limiting examples to enable others of ordinary skill in the art to understand these embodiments and other embodiments involving modifications suited to a particular implementation.

What is claimed is:

1. A method for a cosmetic treatment of skin, comprising:
    applying high-intensity focused ultrasound energy to a skin treatment area of a patient's face, neck or decolletage with simultaneous movement of a transducer body across the skin treatment area including at least one treatment cycle with movement of the transducer body along a first path across the skin treatment area and at least one treatment cycle with movement of the transducer body along a second path across the skin treatment area to form a pattern of interconnected treatment lines in an outer muscle tissue layer at a first depth below a surface of the skin; applying high-intensity focused ultrasound energy to the skin treatment area with simultaneous movement of the transducer body across the skin treatment area including at least one treatment cycle with movement of the transducer body along a third path across the skin treatment area and at least one treatment cycle with movement of the transducer body along a fourth path across the skin treatment area to form a pattern of interconnected treatment lines in a second tissue layer at a second depth below the surface of the skin, wherein the second tissue layer is selected from an epidermis layer, dermis layer, adipose layer, and SMAS layer;
    applying pressure to the patient's skin at one or more pressure points directly above a nerve in or near the skin treatment area during the treatment cycle, wherein the pressure is applied to the patient's skin at the one or more pressure points directly above a nerve using one or more fingers, and wherein the transducer body is held in one hand of an aesthetician and the pressure is applied to the one or more pressure points with the one or more fingers of another hand of the aesthetician; and
    pulling the patient's skin in a direction away from the skin treatment area while maintaining pressure on the one or more pressure points.

2. The method of claim 1, wherein the pattern of interconnected treatment lines is a grid.

3. The method of claim 1, wherein, for each of the treatment cycles, a plurality of treatment lines are formed during the treatment cycle, wherein the plurality of treatment lines are spaced apart relative to a longitudinal axis of the transducer body.

4. The method of claim 3, wherein the plurality of treatment lines are also spaced apart in a direction of the transducer body movement.

5. The method of claim 1, wherein the movement of the transducer body is a continuous movement from a first boundary of the treatment area to an opposing boundary of the treatment area during a fixed duration of the treatment cycle, where the movement begins from the first boundary at initiation of the treatment cycle and the movement ends at the opposing boundary when the treatment cycle automatically ends.

6. The method of claim 1, wherein the transducer body has a longitudinal axis and emits the high-intensity focused ultrasound energy from multiple points along the longitudinal axis, and wherein the longitudinal axis of the transducer body is held perpendicular to a direction of the movement of the transducer body.

7. The method of claim 1, wherein the high-intensity focused ultrasound energy stimulates collagen production along the pattern of interconnected treatment lines in the outer muscle tissue layer and the second tissue layer.

8. The method of claim 1, wherein the high-intensity focused ultrasound energy has a frequency from about 20 MHz to about 500 MHz.

9. The method of claim 1, wherein the high-intensity focused ultrasound energy is focused at a point having a predetermined depth below a skin surface in the skin treatment area.

10. The method of claim 9, wherein the first depth is 4.5 mm and the second depth is selected from 3.0 mm and 1.5 mm.

11. The method of claim 1, further comprising:
    applying high-intensity focused ultrasound energy to the skin treatment area with simultaneous movement of the transducer body across the skin treatment area including at least one treatment cycle with movement of the transducer body along a fifth path across the skin treatment area and at least one treatment cycle with movement of the transducer body along a sixth path across the skin treatment area to form a pattern of interconnected treatment lines in a third tissue layer at a third depth below the surface of the skin, wherein the third tissue layer is selected from an epidermis layer, dermis layer, adipose layer, and SMAS layer, and wherein the third tissue layer is a different layer than the second tissue layer.

12. The method of claim 11, wherein, at each of the first, second and third depths, the pattern of interconnected treatment lines is formed by the movement of the transducer body during a plurality of treatment cycles.

13. The method of claim 12, wherein the pattern of treatment lines is a grid.

14. A method for a cosmetic treatment of skin, comprising:
applying high-intensity focused ultrasound energy to a skin treatment area of a patient's face, neck or decolletage with simultaneous movement of a transducer body across the skin treatment area including at least one treatment cycle with movement of the transducer body along a first path across the skin treatment area and at least one treatment cycle with movement of the transducer body along a second path across the skin treatment area to form a pattern of interconnected treatment lines in an outer muscle tissue layer at a first depth below a surface of the skin;
applying high-intensity focused ultrasound energy to the skin treatment area with simultaneous movement of the transducer body across the skin treatment area including at least one treatment cycle with movement of the transducer body along a third path across the skin treatment area and at least one treatment cycle with movement of the transducer body along a fourth path across the skin treatment area to form a pattern of interconnected treatment lines in a second tissue layer at a second depth below the surface of the skin, wherein the second tissue layer is selected from an epidermis layer, dermis layer, adipose layer, and SMAS layer;
applying pressure to the patient's skin at one or more pressure points directly above a nerve in or near the skin treatment area during the treatment cycle, wherein the pressure is applied to the patient's skin at the one or more pressure points directly above a nerve using one or more fingers, and wherein the transducer body is held in one hand of an aesthetician and the pressure is applied to the one or more pressure points with the one or more fingers of another hand of the aesthetician; and
pulling the patient's skin in a direction toward a root of the nerve while maintaining pressure on the one or more pressure points.

15. The method of claim 1, wherein ultrasound stimulation of the muscle tissue layer in the vicinity of a lymphatic node that is being obstructed by pressure from the muscle tissue layer causes the muscle tissue layer to return to a more youthful position and open the lymphatic node.

16. The method of claim 14, further comprising:
massaging the skin treatment area over a lymphatic node in a direction that the lymphatic node drains.

17. The method of claim 14, wherein the pattern of interconnected treatment lines is a grid.

18. The method of claim 14, wherein, for each of the treatment cycles, a plurality of treatment lines are formed during the treatment cycle, wherein the plurality of treatment lines are spaced apart relative to a longitudinal axis of the transducer body, and wherein the plurality of treatment lines are also spaced apart in a direction of the transducer body movement.

19. The method of claim 14, wherein the movement of the transducer body is a continuous movement from a first boundary of the treatment area to an opposing boundary of the treatment area during a fixed duration of the treatment cycle, where the movement begins from the first boundary at initiation of the treatment cycle and the movement ends at the opposing boundary when the treatment cycle automatically ends.

20. The method of claim 14, wherein the transducer body has a longitudinal axis and emits the high-intensity focused ultrasound energy from multiple points along the longitudinal axis, and wherein the longitudinal axis of the transducer body is held perpendicular to a direction of the movement of the transducer body.

* * * * *